( 12 ) United States Patent
Bankowski

(10) Patent No.: US 10,494,325 B2
(45) Date of Patent: Dec. 3, 2019

(54) METHOD OF INDUSTRIALLY PRODUCING MONOCHLOROACETIC ACID

(71) Applicant: PCC MCAA SP. Z O.O., Brzeg Dolny (PL)

(72) Inventor: Bartosz Bankowski, Wroclaw (PL)

(73) Assignee: PCC MCAA SP. Z O. O., Brzeg Dolny (PL)

( * ) Notice: Subject to any disclaimer, the term of this patent is extended or adjusted under 35 U.S.C. 154(b) by 0 days.

(21) Appl. No.: 16/074,472

(22) PCT Filed: Feb. 4, 2017

(86) PCT No.: PCT/PL2017/050006
§ 371 (c)(1),
(2) Date: Aug. 1, 2018

(87) PCT Pub. No.: WO2017/135832
PCT Pub. Date: Aug. 10, 2017

(65) Prior Publication Data
US 2019/0039986 A1    Feb. 7, 2019

(30) Foreign Application Priority Data
Feb. 4, 2016  (PL) .......................................... 416027

(51) Int. Cl.
*C07C 51/363*    (2006.01)
*C07C 51/44*    (2006.01)
(52) U.S. Cl.
CPC ............ *C07C 51/363* (2013.01); *C07C 51/44* (2013.01)
(58) Field of Classification Search
CPC ............................... C07C 51/363; C07C 51/44
See application file for complete search history.

(56) References Cited

U.S. PATENT DOCUMENTS

| 2,688,634 A | 9/1954 | Pinkston, Jr. |
| 5,756,840 A | 5/1998 | Ebmeyer et al. |
| 2005/0272953 A1 | 12/2005 | Crouzen et al. |

FOREIGN PATENT DOCUMENTS

| CN | 102274708 A | 12/2011 |
| CN | 104649887 A | 5/2015 |

(Continued)

OTHER PUBLICATIONS

International Search Report and Written Opinion issued in corresponding International Patent Application No. PCT/PL2017/050006 dated May 31, 2017 (10 pages).

*Primary Examiner* — Yate' K Cutliff
(74) *Attorney, Agent, or Firm* — Kilyk & Bowersox, P.L.L.C.

(57) ABSTRACT

A method of producing monochloroacetic acid (MCAA) has been disclosed encompassing (a) a stage of the direct chlorination of acetic acid with chlorine and (b) a stage of recovery of the catalyst in the form of acid chlorides from the reaction mixture before (c) a hydrodehalogenation stage characterized by the fact that the chlorination process (a) is conducted at the boiling temperature of the mixture under a pressure of 0-1.0 barg, in an excess of acetic acid with respect to the dosed chlorine gas, while the heat from the reaction is taken off mainly through the evaporation of volatile components of the mixture, followed by their condensation in the reflux condenser above the reactor and the return to the chlorination reaction, after which the reaction mixture containing monochloroacetic acid, acetic acid, dichloroacetic acid and optionally acid chlorides which are present in the mixture and, optionally, anhydrides of these acids, is feed to the vacuum distillation process (b), which is conducted continuously in the distillation column in a vacuum of 0 to 500 mbar from which volatile components of the mixture, mainly acid chlorides, as well as some acetic (Continued)

Figure 1:
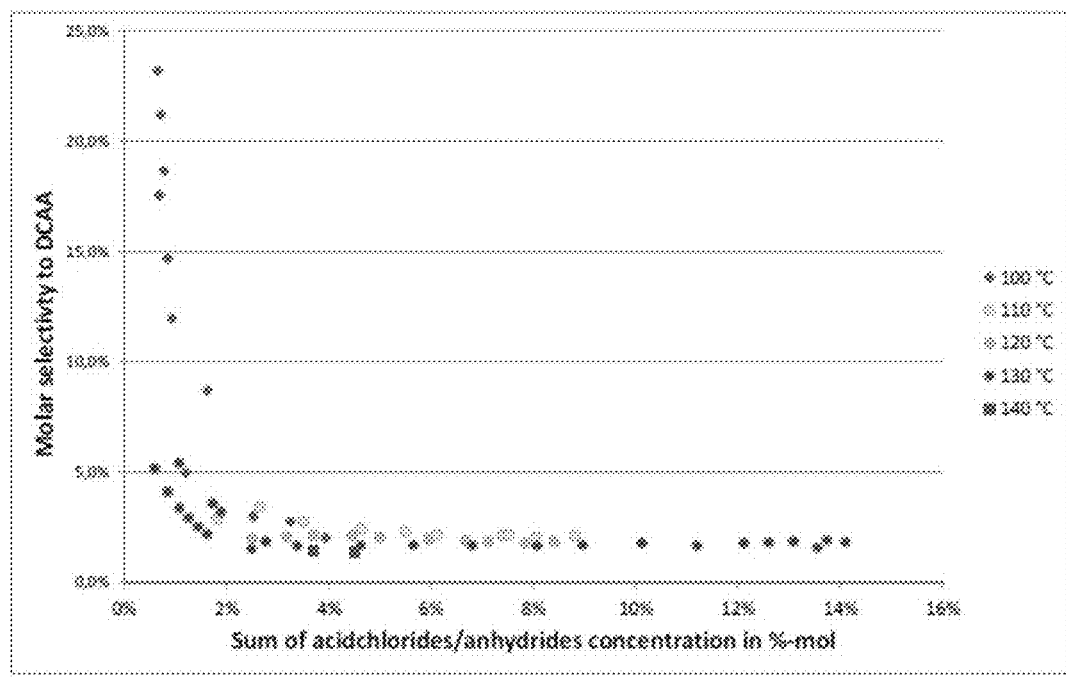

acid and some monochloroacetic acid are taken off as distillate and returned to the chlorination process as a result of which the catalyst of the chlorination is almost completely recovered.

9 Claims, 2 Drawing Sheets

(56) References Cited

FOREIGN PATENT DOCUMENTS

| | | | |
|---|---|---|---|
| CN | 105130786 | A | 12/2015 |
| CN | 106242961 | A | 12/2016 |
| NL | 109769 | C | 10/1964 |
| WO | 2013057125 | A1 | 4/2013 |
| WO | 2017135833 | A1 | 8/2017 |

METHOD OF INDUSTRIALLY PRODUCING MONOCHLOROACETIC ACID

This application is a National Stage Application of PCT/PL2017/050006, filed Feb. 4, 2017, which claims priority to Polish Patent Application No. P.416027, filed Feb. 4, 2016.

The subject matter of the invention is an improved method of producing monochloroacetic acid (MCAA), in which the product is obtained by direct chlorination of acetic acid (stage I) with chlorine gas in the presence of a chlorinating catalyst. The method according to the invention is used for industrially producing MCAA.

The method of producing raw monochloroacetic acid (MCAA) most commonly used in industry is direct chlorination of acetic acid with chlorine gas in the presence of a homogeneous catalyst at increased pressure:

$$CH_3COOH+Cl_2=CH_2ClCOOH+HCl$$

The reaction takes place in a reactor in the liquid phase at a pressure of 3-5 barg. The reaction mixture is saturated with chlorine gas which is dissolved in the liquid phase, in waterless conditions.

The catalysts in the process are the acetic acid chloride ($CH_3COCl$) and chloroacetic acid chloride ($ClCH_2COCl$), which are usually formed in-situ from acetic anhydride, which is added precisely because it is a precursor of acid chlorides. Hydrogen chloride which is produced during the reaction, causes the conversion of the anhydride to acid chloride and acetic acid.

The following reactions take place during chlorination:

$$(CH_3CO)_2O+HCl=CH_3COOH+CH_3COCl \text{ (formation of acetyl chloride)}$$

$$CH_3COCl+Cl_2=ClCH_2COCl+HCl \text{ (reaction of acetyl chloride with chlorine to chloroacetyl chloride)}$$

$$ClCH_2COCl+CH_3COOH=ClCH_2COOH+CH_3COCl \text{ (reaction of chloroacetyl chloride to MCAA)}$$

$$ClCH_2COCl+Cl_2=Cl_2CHCOCl+HCl \text{ (formation of dichloroacetyl chloride)}$$

$$ClCH_2COCl+ClCH_2COOH=Cl_2CHCOOH+CH_3COCl \text{ (reaction of MCAA and acetyl chloride to dichloroacetic acid)}$$

$$Cl_2CHCOCl+CH_3COOH=Cl_2CHCOOH+CH_3COCl \text{ (production of DCAA from dichloroacetyl chloride)}$$

$$ClCH_2COOH+Cl_2CHCOCl=Cl_2CHCOOH+ClCH_2COCl \text{ (reaction of MCAA with dichloroacetyl chloride to DCAA).}$$

In accordance with U.S. Pat. No. 7,135,597, the pressure above the surface of the liquid should typically be between 3 and 5 barg in the chlorination reaction of acetic acid, while the temperature should lie within the range of 115 to 155° C. However, the process run in such conditions causes problems with the maintenance of the integrity of the installation and, consequently, corrosion of the apparatus and piping. The biggest threat is HCl gas saturated with acid chlorides which create a highly corrosive environment.

As the chlorination reaction is strongly exothermic, the energy given off during this process must be removed. Among the known methods, the majority of the heat is discharged by the reactor cooling system, such as a jacket fed with cooling water. The known method of chlorination requires the use of large circuits of cooling media and the maintenance of an appropriately small difference in temperature in the reaction and in the reactor's jacket. In addition, due to interference in mixing and restrictions on the transfer of heat, which are almost unavoidable in industrial conditions, the use of a heat removal reaction using the reactor's cooler through the external cooling jacket fed with cooling water gives rise to the risk of local excessive cooling of the reaction mixture and the damping of the reaction near the reactor's jacket.

Heat distribution can be improved in the reactor by using an agitator (U.S. Pat. No. 2,688,634), although, all the more, such a solution makes it difficult to maintain the tightness of the reaction system, while the agitator's drive and the other devices are exposed to the continuous operation of factors which are extremely corrosive. It is virtually impossible to seal the reactor system if a mechanical agitator is used.

As a result, the whole of the chlorine node requires very precise control and the use of special automation systems. However, this does not rule out the risk of losing control of the reaction at the time a failure arises in the feed of cooling water to the reactor jacket.

The objective of this invention is to avoid the problems described above which appear in the industrial production of MCAA, in particular the exclusion of inconvenience and risks related to the use of the reactor coolant system and the agitator of the reaction mixture.

It was possible to unexpectedly achieve the objective defined above in a manner according to the invention.

The subject matter of the invention is the method of production of monochloroacetic acid (MCAA) encompassing (a) the stage of direct chlorination of acetic acid with chlorine and (b) the stage of recovery of the catalyst in the form of acid chlorides from the reaction mixture before (c) the hydrodehalogenation stage, characterized by the fact that:

a. the chlorination process is conducted in a flow reactor in boiling conditions under pressure of between 0 and 1 barg, whereby the temperature in the reactor is between 100 and 130° C., while the heat from the reaction is fundamentally taken off to an equal extent from the whole of the volume of the reacting liquid through the evaporation of components of the mixture as a result of its boiling, after which the gaseous effluents from the chlorination condense in the condenser fed with a refrigerant and return to the chlorination process, whereby the gaseous effluents in the condenser are cooled to such an extent that the gaseous phase has a temperature at the output from the cooler of no more than 70° C., b. the catalyst is recovered from the chlorination with the reaction mixture obtained in stage (a) through distillation under reduced pressure in the vacuum column, while the acid chlorides obtained after distilling condense and return to the chlorination process (a), whereby the mixture of acid chlorides and acetic acid and possibly monochloroacetic acid is taken off as a distillate, whereby the temperature at the top of the column is between 65 and 85° C., while the temperature in the bottom of the column is between 110 and 130° C., c. the remaining liquid is subjected to hydrodehalogenation using a known method and monochloroacetic acid is obtained.

Preferably, in stage (a), the concentration of the catalyst in the reaction mixture is approximately 4% mol.

Preferably, in stage (a) the chlorination process is conducted under pressure of between 0.1 and 0.8 barg, especially preferably from 0.2 to 0.4 barg.

Preferably, the reaction mixture obtained in stage (a), which is simultaneously the feed for vacuum distillation in stage (b), contains a minimum of 50% by weight of monochloroacetic acid, a maximum of 35% acetic acid, from 2 to 5% acetyl chloride and from 1 to 4% chloroacetyl chloride.

Preferably, in stage (b), gaseous hydrogen chloride is added to the vacuum pre-distillation column to convert the acid anhydrides into appropriate acid chlorides, whereby the ratio of the mass of hydrogen chloride to the mass of reaction mixture feeding the column is no greater than 1:20 (i.e. a maximum of 1 part HCl to 20 parts mixture constituting the feed to stage b).

Preferably, the temperature of the feed (the product stream) added to the initial vacuum distillation column is in the range of 60 to 130° C., preferably from 100 to 120° C.

Especially preferably, the feed (product stream) obtained through chlorination in stage a) and fed to the vacuum distillation column in stage b) has a temperature which is higher than the temperature of the theoretical plate to which it is passed, which results in the immediate expansion of the feed and the evaporation of part of the liquid upon entry into the column.

In order to better present this invention, its description has been supplemented by the following examples of implementation, and the following diagrams:

FIG. 1 presents the dependence of the concentration of DCAA in the product on the concentration of the catalyst during the chlorination of acetic acid.

Figure 2:
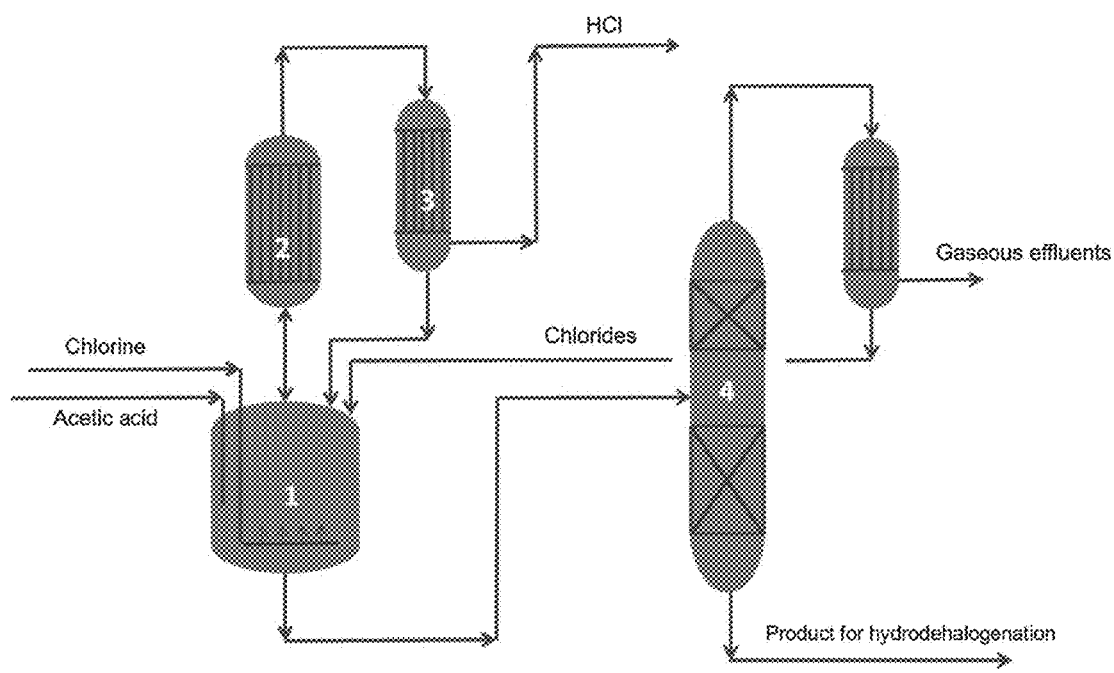

FIG. 2 presents a sketch of the system for implementing the method according to the invention, whereby 1 is the chlorination reactor, 2—the reflux condenser, 3—the deep cooling system and 4—the vacuum distillation column.

However, the examples below should not be equated to the full extent of this invention, the essence of which has been specified above.

DETAILED DESCRIPTION OF THE INVENTION

This invention is based on the fact that the chlorination process is conducted at a pressure which is close to atmospheric pressure and at a boiling temperature of the process liquid, while the whole or the majority of the heat from the reaction is taken off from the system of the chlorination process through the evaporation of the mixture and condensation of the vapours in the reflux condenser located above the reactor, by which the majority of the evaporated mass returns directly to the reaction environment after condensation.

It was unexpectedly found that the chlorination stage can be conducted with excess acetic acid with respect to chlorine and in conditions of boiling of the process liquid, as a result of which ideal heat distribution is obtained in the process mixture without the use of any additional mixing methods.

Therefore, in the method according to the invention, there is no need to use agitators for the reaction mixture which enables the elimination of known risks and inconveniences related to the use of this element.

Furthermore, it was unexpectedly established that conducting the chlorination process under a pressure which is close to atmospheric pressure means that a significant volumetric flow of hydrogen chloride gas is obtained. This gas is saturated with vapours of compounds which are present in the reaction mixture.

The quantity of compounds taken off from the gaseous phase also depends on the volume of passing hydrogen chloride, their share of the reaction mixture and primarily their vapour pressure.

Most of the heat from the chlorination reaction is consumed by the phase transformation of the emerging gaseous effluents.

As a result, in the method according to the invention, there is no need to cool the reactor with a jacket, while the system of condensation of the gaseous effluents is adapted to accept the whole of the mass which has evaporated.

Therefore, in the method according to the invention, there is no need to use a reactor cooling system which enables the elimination of known risks and inconveniences related to the use of this system.

As a result, the solution according to the invention minimizes the risk of damage to the apparatus from the shutdown of the reactor cooler, the overheating of the reaction mass and the temporary loss of control of the chlorination process. The return cooler is responsible for the condensation of the majority of components of the gaseous mixture. The uncondensed residues are condensed in a deep cooling system, where the remaining uncondensed fractions—mainly acetyl chloride—condense and flow by gravity to the chlorination process.

In the methods of synthesis known from the state of the art, which are conducted at a higher pressure, it is relatively easy to maintain a relatively high concentration of catalyst in the reactor, which, as supposed, should assure an appropriate course of the reaction.

In this invention, it was unexpectedly found that, while conducting the process in a pressure which is close to atmospheric and at the boiling point of the mixture, where the chlorides continuously return to the process, the concentration of the catalyst is approximately 4% mol. It was also established that the selectivity of the chlorination process does not increase with the increase in the concentration of chlorides above 4% mol. (FIG. 1). It was unexpectedly found that a reduction in pressure during chlorination does not adversely affect the course of the reaction, although it helps significantly improve the take-off of the heat as a result of the effect of evaporation of volatile components of the mixture and their condensation in the return cooler.

Importantly, the take-off of the heat through the evaporation of the volatile components of the process liquid in boiling conditions guarantees an identical temperature in the whole of the volume of liquid and the inability to cool the reaction until its slows down or ends. The system according to the invention can be described as self-regulating.

In the method according to the invention, the process should be controlled, especially the degree of cooling of the gaseous effluents. The temperature of the gaseous effluents at the output from the return cooler should be maintained to ensure that only hydrogen chloride and acid chlorides are present in the gaseous phase, while all the other components, such as MCAA and acetic acid are condensed and flow down gravitationally to the reactor. In the method according to the invention, the temperature at the top of the return coolers should not exceed 70° C., it should preferably not exceed 50° C., especially preferably, it should not exceed 35° C.

As a result, the method of conducting the chlorination process according to the invention also allows for a significant reduction in the consumption of refrigerants for freezing the volatile fractions from the chlorination.

Conducting the chlorination process according to the invention with an excess of acetic acid with respect to chlorine enables the achievement of a full conversion of chlorine into the products of the reaction. As a result, the purification of the waste gases, the main component of which is HCl, is much simpler and less expensive than in the case of known solutions, because it boils down to the condensation of only acid chlorides in a low temperature without the need to recover the chlorine or accept losses of this raw material.

The use of a relatively low pressure in the chlorination reactor and the process gas purification system in the method according to the invention means that it is easier to maintain tightness of flanged connections of the process apparatus and therefore to reduce the risk of corrosion. In the method according to the invention, the composition of the liquid as well as the vapour is completely different than in the case of processes conducted at a higher pressure. As a result of the significant evaporation of chlorides from the mixture, the concentration of anhydrides is also reduced because the chlorides 4 anhydrides equilibrium moves towards the chlorides, which is also affected by a large excess of hydrogen chloride in the reaction environment.

After the chlorination stage, the reaction mixture usually still contains significant quantities of acid chlorides, which need to be separated from the raw product and returned to the process. Separation is usually conducted through stripping of the reaction mixture using dry hydrogen chloride gas which is free of acid chlorides and anhydrides. The process is conducted in a stripping column at atmospheric pressure (U.S. Pat. No. 2,688,634) or increased pressure (WO 2013/057125 A1), after which acetyl chloride is condensed or absorbed in fresh acetic acid constituting the feed to the chlorination process. Stripping with hydrogen chloride gas naturally results in the shift of equilibrium of the acid chlorides→acid anhydrides reaction towards the acid chlorides. Most of the chlorides are blown out with hydrogen chloride, while the remnants are easily hydrolysed with water, as a result of which a mixture which is devoid of chlorides, which are inhibitors of the reaction, which takes place in the next stage of the process—catalytic hydrodehalogenation. However, the result of the equilibrium shift towards chlorides in the process conducted at atmospheric pressure (U.S. Pat. No. 2,688,634) is virtually unnoticeable and the product sent to hydrodehalogenation will contain acid anhydrides formed from the chlorides, causing the formation of hard-to-remove polymeric impurities.

The increased pressure used in methods known from the state of the art (WO 2013/057125 A1) allows for a much more noticeable shift of the equilibrium of the acid chlorides→acid anhydrides reaction towards the chlorides, as the release of hydrogen chloride—the only gaseous product in the reaction of chlorides to anhydrides—is impeded. However, just as at the chlorination stage, increased pressure significantly increases the risk of failure due to leaks and damage to the apparatus under the influence of corrosion caused by extremely acidic substances. The disadvantage of the known method of recovering acid chlorides is the fact that, due to the high pressure used in the state of the art, it is difficult for the acid chlorides to evaporate off from the liquid being stripped. Therefore, a significant proportion of the chlorides remain in the raw product sent for hydrodehalogenation. Before entering the hydrodehalogenation reactors, the mixture is admittedly subjected to hydrolysis with water to destroy the chlorides, but the fact that there are far more than in the process conducted at a low pressure means that the catalyst losses are greater than in the method according to the invention.

In accordance with the invention, the chlorination catalyst is recovered by vacuum distillation, which, preferably, may be assisted by a slight flow of hydrogen chloride. During the analysis of the process of recovering chlorides, it was unexpectedly found that a significant improvement in the efficiency of the process is achieved through the evaporation of chlorides under reduced pressure. For this purpose, in accordance with the preferable implementation of the invention, the mixture from chlorination is introduced continuously into the vacuum distillation column, which has a pressure of between −0.9 and −0.4 bar(g). In the preferable implementation of the invention, the liquid is introduced into the column at such a height which has a temperature enabling the immediate evaporation of volatile fractions of the mixture (so-called flash feed) and their discharge at the top of the column. In order to enable the separation of the evaporated chlorides, namely the gaseous phase from the liquid phase, the section of the column to which the raw mixture is introduced is preferably a section which is not filled, whereas the beds of the column are above (distillation bed) and below (stripping bed) the empty section to which the mixture is injected. The distillation bed serves the purpose of washing the acid chlorides of fractions with higher boiling points (MCAA, acetic acid) while the stripping bed is used to vaporize the residual low boiling point chlorides from the liquid phase.

It should be noted that the solution proposed in the preferred implementation of the invention enables the removal of the chlorides from the process mixture constituting the feed for hydrogenation very quickly, before they can be converted to anhydrides. Of course, the acid chlorides are partially converted into anhydrides after condensing in the distillate tank as it contains a significant quantity of acids. However, this is irrelevant to the process, because, even so, it is all returned to the chlorination process where the anhydrides are converted in the excess HCl into chlorides and then chlorinated to MCAA.

Preferably, vacuum distillation may be conducted as such, without the intervention of auxiliary materials, or equally preferably, in a hydrogen chloride atmosphere, a small addition of which can be additionally injected to further shift the equilibrium towards the acid chlorides.

In addition, initially, before vacuum distillation, some of the chlorides may be preferably removed from the liquid by way of rapid evaporation as a result of expansion in the evaporator (pre-flash) or a series of vacuum evaporators, which can have the same temperature and pressure, or these parameters can vary in each of them depending on the composition of the liquid entering each successive evaporator.

The vacuum can be produced in the column with any type of vacuum pump, for example, a water ring pump, a dry vacuum pump or, for example, a piston pump. A preferred solution is also a liquid jet vacuum pump driven by one of the liquid media appearing in the production process, for instance, water or one of the raw materials.

Preferably, hydrogen chloride is dosed from the bottom of the distillation column, while its role is also to shift the equilibrium of the chlorides-anhydrides reaction towards the chlorides, which are taken off as distillate. Even so, hydrogen chloride only has an auxiliary role in the process because most of the chlorides should be immediately evaporated at the initial stage of the distillation.

Likewise, at this stage, the pressure prevailing in the process is important. The vacuum used in the preferred implementation of the invention means there is no threat of the system experiencing a leak nor the emission of hydrogen chloride and vapours of the process mixture what would cause immediate corrosion of the apparatus.

A production process of monochloroacetic acid by means of direct chlorination of acetic acid with chlorine gas is revealed in the method known from U.S. Pat. No. 2,688,634, whereby the use of reflux condenser for condensing chlorides from the process gaseous effluents from the chlorination is described, although the excess chlorine is used and a chlorination reaction is conducted to obtain the greatest possible degree of reaction. Compared with the method known from the state of the art, the advantage of this invention is that the use of excess acetic acid with respect to chlorine makes it easier treating of gaseous effluents from the process by eliminating unreacted chlorine from the off gases. However, the advantage of this invention is primarily that the chlorination reaction is conducted at the boiling temperature of the process mixture, which stabilizes the temperature of the process and improves the heat and mass transfer.

Example 1

4 dm$^3$ of a mixture containing 98% acetic acid and 2% acetic anhydride was placed into a glass reactor [R01] in the form of a glass cylinder with an internal diameter of 13 cm, height 60 cm, as well as with a heating jacket and equipped with a dip pipe ending in a sparger with sintered glass, and then 83 g acetyl chloride was added. The reaction system was built as in diagram 1. A reflux condenser [E03] fed with cold water was placed above the reactor. The gaseous effluents not condensed in the reflux condenser were cooled to −20° C. in the next stage [E04], where the refrigerant was a commercially available refrigerant in the form of a mixture of hydrocarbons. The condensate from the second stage was collected in the tank [T05] and dosed back to the chlorination reactor.

After placing the solution in the reactor, its content was heated to 80° C. and chlorine started to be introduced into the reaction environment through the sparger. The intensity of the chlorine flow was gradually increased and in the remainder of the chlorination process, it was kept within the range of 1.0 to 1.2 kg/h. The temperature in the reactor settled at 118-120.5° C. The composition of the reaction mixture was determined with the NIR (near infra-red) and gas chromatography methods.

The concentration of chlorine in the gaseous effluents to the HCl scrubber was continuously monitored with UV spectroscopy.

After two hours from the start of the reaction, the acetic acid and anhydride mixture started to be continuously dosed in the previously presented proportions and at a flow rate of the order of 1400 cm$^3$/h.

At the same time, the product started to be taken off, the flow rate of which was determined such that the level of liquid in the reactor did not change (approximately 2 dm$^3$/h). The composition of the mixture leaving the reactor was as follows: acetic acid 31.0-32.0%, MCAA 60.1-61.32%, DCAA 3.65-3.78%, acetyl chloride 2.35-2.5%, dichloroacetyl chloride 1.31-1.43%, chloroacetic-acetic anhydride 240-290 ppm, acetic anhydride 300 ppm. The HCl content was about 0.4%.

The reaction mixture from the chlorination was added continuously to the distillation column, in which a pressure around 0.5 bar(a) was maintained. Hydrogen chloride gas from a cylinder was dosed into the bottom of the column. The HCl flow during the first two hours of distillation was approximately 63-66 litres/h. The product from bottom of the column was analysed using the GC-FID and GC-ECD method. Samples were taken every 15 minutes and analysed without derivatisation.

The liquid taken from the distillation column contained from 26.9 to 28% acetic acid, approximately 67-68% MCAA, between 4 and 4.4% DCAA and 58-160 ppm acetyl chloride, 0.36-0.54% chloroacdddetyl chloride, 380-460 ppm dichloroacetyl chloride and 430 to 610 ppm chloroacetic-acetic anhydride.

After two hours from the start of the distillation, the HCl flow was reduced to 13-15 litres/hour.

Samples were taken in the same time intervals as previously.

The analyses showed that the composition of the mixture taken from the bottom of the column only differed slightly in terms of concentrations of chlorides and anhydrides. The mixture contained less than 100 ppm acetyl chloride, 0.1-0.12% chloroacetyl chloride, 180-230 ppm dichloroacetyl chloride, as well as 0.3 to 0.51% chloroacetic-acetic anhydride and 70-110 ppm acetic anhydride.

The distillate contained 1.2% HCl, 72% acetic acid, 0.22% acetic anhydride, 16.23% acetyl chloride, 8.4% chloroacetyl chloride, 0.28% dichloroacetyl chloride, 0.995% MCAA and 0.31% DCAA.

The invention claimed is:

1. A method for production of monochloroacetic acid (MCAA) said method comprising
   a. conducting a chlorination process of acetic acid with chlorine with a chlorination catalyst in a flow reactor in boiling conditions under pressure of between 0 and 1 barg, to form a reaction mixture whereby a temperature in the flow reactor is between 100 and 130° C., with heat of reaction being taken off by evaporation of gaseous effluents and performing a chlorination condensing in a reflux condenser to obtain condensed gaseous effluents and returning the condensed gaseous effluents to the chlorination process, whereby the gaseous effluents in the reflux condenser are cooled such that the gaseous phase has a temperature at the output of no more than 70° C.,
   b. recovering the chlorination catalyst as acid chlorides from the reaction mixture obtained in stage (a) through a vacuum distillation in a vacuum column, where the acid chlorides condense and return the acid chlorides to the flow reactor for the chlorination process, and separating whereby as a distillate, a mixture of acid chlorides and acetic acid and optionally monochloroacetic acid from remaining liquid, whereby a temperature at a top of the vacuum column is between 65 and 85° C., while a temperature in a bottom of the vacuum column is between 110 and 130° C., and then
   c. subjecting the remaining liquid to hydrodehalogenation to obtain said monochloroacetic acid.

2. The method according to claim 1, wherein in stage (a), the chlorination catalyst in the reaction mixture has a concentration of approximately 4% mol.

3. The method according to claim 1, wherein in stage (a), the chlorination process is conducted under pressure of between 0.1 and 0.8 barg.

4. The method according to claim 1, wherein the reaction mixture obtained in stage (a) contains a minimum of 50% by weight of monochloroacetic acid, a maximum of 35% by weight acetic acid, from 2 to 5% by weight acetyl chloride and from 1 to 4% by weight chloroacetyl chloride.

5. The method according to claim 1, wherein in stage (b), said method further comprising adding hydrogen chloride gas to the vacuum column, whereby the ratio of the mass of hydrogen chloride gas which is dosed to the mass of reaction mixture is not greater than 1:20.

6. The method according to claim 1, wherein a temperature of the reaction mixture added to the vacuum column is in the range of 60 to 130° C.

7. The method according to claim 6, wherein the reaction mixture obtained in stage a) and fed to the vacuum column in stage b) has a temperature higher than the temperature of the theoretical plate to which it is introduced.

8. The method according to claim 1, wherein in stage (a), the chlorination process is conducted under pressure of from 0.2 to 0.4 barg.

9. The method according to claim 1, wherein a temperature of the reaction mixture added to the vacuum column is in the range of from 100 to 120° C.

* * * * *